(12) United States Patent
Moskowitz et al.

(10) Patent No.: US 10,537,367 B2
(45) Date of Patent: Jan. 21, 2020

(54) BIDIRECTIONAL FIXATING INTERVERTEBRAL IMPLANT SYSTEM

(71) Applicant: Moskowitz Family LLC, Rockville, MD (US)

(72) Inventors: Nathan C. Moskowitz, Rockville, MD (US); Mosheh T. Moskowitz, Rockville, MD (US); Daniel Glozman, Kefar Adummim (IL)

(73) Assignee: Moskowitz Family LLC, Rockville, MD (US)

( * ) Notice: Subject to any disclaimer, the term of this patent is extended or adjusted under 35 U.S.C. 154(b) by 0 days.

(21) Appl. No.: 15/934,614

(22) Filed: Mar. 23, 2018

(65) Prior Publication Data

US 2018/0235672 A1 Aug. 23, 2018

Related U.S. Application Data

(60) Continuation of application No. 14/299,711, filed on Jun. 9, 2014, now Pat. No. 10,016,225, which is a
(Continued)

(51) Int. Cl.
*A61B 17/064* (2006.01)
*A61B 17/068* (2006.01)
(Continued)

(52) U.S. Cl.
CPC ........ *A61B 17/7064* (2013.01); *A61B 17/068* (2013.01); *A61B 17/0642* (2013.01);
(Continued)

(58) Field of Classification Search
CPC ............ A61B 17/7064; A61B 17/0642; A61B 17/068; A61B 17/70; A61B 2017/0648;
(Continued)

(56) References Cited

U.S. PATENT DOCUMENTS 4,064,881 A 12/1977 Meredith
4,554,914 A 11/1985 Kapp et al.
(Continued)

FOREIGN PATENT DOCUMENTS

WO 2004093749 11/2004
WO 2006091503 8/2006

OTHER PUBLICATIONS

Vincent C. Traynelis, "Prosthetics and Biologics: The Wave of the Future," Clinical Neurosurgery, vol. 50, Proceedings of the Congress of Neurological Surgeons, Philadelphia, PA 2002, Chapter 9, pp. 207-219.
(Continued)

*Primary Examiner* — Pedro Philogene
(74) *Attorney, Agent, or Firm* — Fish & Richardson P.C.

(57) ABSTRACT

A bidirectional fixating intervertebral implant system includes at least one implant body, a perimeter enclosure, and first and second anchors. The at least one implant body has first and second vertebral body-facing surfaces with first and second sets of ridges. The first and second vertebral body-facing surfaces define first and second anchor openings. The perimeter enclosure extends around a body perimeter of the implant body. The implant body and the perimeter enclosure are sized to fit within a disc space. The perimeter enclosure defines at least one tool hole. The first and second anchors are sized and configured to extend through the first and second anchor openings. The first and second anchors have first and second shaft portions and first and second vertebral body engagement portions extending laterally outward from the first and second shaft portions, respectively, in multiple directions.

20 Claims, 18 Drawing Sheets

Related U.S. Application Data continuation of application No. 12/868,451, filed on Aug. 25, 2010, now Pat. No. 8,747,444, which is a division of application No. 11/536,815, filed on Sep. 29, 2006, now Pat. No. 7,846,188, which is a continuation-in-part of application No. 11/208,644, filed on Aug. 23, 2005, now Pat. No. 7,704,279.

(60) Provisional application No. 60/670,231, filed on Apr. 12, 2005.

(51) Int. Cl.
  *A61B 17/70* (2006.01)
  *A61F 2/30* (2006.01)
  *A61F 2/44* (2006.01)
  *A61F 2/46* (2006.01)

(52) U.S. Cl.
  CPC ............ *A61B 17/70* (2013.01); *A61F 2/4455* (2013.01); *A61F 2/4611* (2013.01); *A61B 2017/0648* (2013.01); *A61F 2/442* (2013.01); *A61F 2/4405* (2013.01); *A61F 2002/30507* (2013.01); *A61F 2002/30517* (2013.01); *A61F 2002/30525* (2013.01); *A61F 2002/30579* (2013.01); *A61F 2002/30828* (2013.01); *A61F 2002/30841* (2013.01); *A61F 2002/30904* (2013.01); *A61F 2002/448* (2013.01); *A61F 2002/4627* (2013.01); *A61F 2002/4628* (2013.01); *A61F 2220/0025* (2013.01); *A61F 2310/00023* (2013.01); *A61F 2310/00029* (2013.01)

(58) Field of Classification Search
  CPC .... A61F 2/4455; A61F 2/4611; A61F 2/4405; A61F 2/442; A61F 2/447; A61F 2002/30507; A61F 2002/30517; A61F 2002/30525; A61F 2002/30579; A61F 2002/30828; A61F 2002/30841; A61F 2002/30904; A61F 2002/448; A61F 2002/4627; A61F 2002/4628; A61F 2220/0025; A61F 2310/00023; A61F 2310/00029
  USPC .... 606/246–279, 300–328; 623/17.11–17.16
  See application file for complete search history.

(56) References Cited

U.S. PATENT DOCUMENTS

| | | |
|---|---|---|
| 4,599,086 A | 7/1986 | Doty |
| 4,636,217 A | 1/1987 | Ogilvie et al. |
| 4,960,420 A | 10/1990 | Goble et al. |
| 4,997,432 A | 3/1991 | Keller |
| 5,005,749 A | 4/1991 | Aranyi |
| 5,062,850 A | 11/1991 | MacMillan et al. |
| 5,123,926 A | 6/1992 | Pisharodi |
| 5,290,312 A | 3/1994 | Kojimoto et al. |
| 5,405,391 A | 4/1995 | Henderson et al. |
| 5,413,583 A | 5/1995 | Wohlers |
| 5,454,819 A | 10/1995 | Knoepfler |
| 5,514,180 A | 5/1996 | Heggeness et al. |
| 5,660,188 A | 8/1997 | Groiso |
| 5,667,472 A | 9/1997 | Finn et al. |
| 5,713,912 A | 2/1998 | Porter |
| 5,782,832 A | 7/1998 | Larsen et al. |
| 5,860,973 A | 1/1999 | Michelson |
| 5,865,848 A | 2/1999 | Baker |
| 5,868,759 A | 2/1999 | Peyser |
| 5,888,223 A | 3/1999 | Bray, Jr. |
| 5,916,224 A | 6/1999 | Esplin |
| 5,951,574 A | 9/1999 | Stefanchik et al. |
| 5,960,522 A | 10/1999 | Boe |
| 5,968,054 A | 10/1999 | Yeatts et al. |
| 5,976,136 A | 11/1999 | Bailey et al. |
| 6,126,689 A | 10/2000 | Brett |
| 6,342,074 B1 | 1/2002 | Simpson |
| 6,368,350 B1 | 4/2002 | Erickson et al. |
| 6,375,682 B1 | 4/2002 | Fleischmann et al. |
| 6,419,704 B1 | 7/2002 | Ferree |
| 6,432,106 B1 | 8/2002 | Fraser |
| 6,458,159 B1 | 10/2002 | Thalgott |
| 6,527,804 B1 | 3/2003 | Gauchet et al. |
| 6,533,818 B1 | 3/2003 | Weber et al. |
| 6,558,423 B1 | 5/2003 | Michelson |
| 6,572,653 B1 | 6/2003 | Simonson |
| 6,579,318 B2 | 6/2003 | Varga et al. |
| 6,582,468 B1 | 6/2003 | Gauchet |
| 6,613,055 B2 | 9/2003 | Di Emidio |
| 6,629,998 B1 | 10/2003 | Lin |
| 6,641,614 B1 | 11/2003 | Wagner et al. |
| 6,719,794 B2 | 4/2004 | Gelber |
| 6,723,126 B1 | 4/2004 | Berry |
| 6,733,532 B1 | 5/2004 | Gauchet et al. |
| 6,764,491 B2 | 7/2004 | Frey et al. |
| 6,770,094 B2 | 8/2004 | Fehling et al. |
| 6,824,564 B2 | 11/2004 | Crozet |
| 6,852,117 B2 | 2/2005 | Orlowski |
| 6,904,308 B2 | 6/2005 | Frisch et al. |
| 6,953,477 B2 | 10/2005 | Berry |
| 6,955,671 B2 | 10/2005 | Uchikubo |
| 6,972,019 B2 | 12/2005 | Michelson |
| 7,030,904 B2 | 4/2006 | Adair et al. |
| 7,033,394 B2 | 4/2006 | Michelson |
| 7,037,258 B2 | 5/2006 | Chatenever et al. |
| 7,060,073 B2 | 6/2006 | Frey et al. |
| 7,097,615 B2 | 8/2006 | Banik et al. |
| 7,211,112 B2 | 5/2007 | Baynham et al. |
| 7,326,248 B2 | 2/2008 | Michelson |
| 7,442,209 B2 | 10/2008 | Michelson |
| 7,615,059 B2 | 11/2009 | Watschke et al. |
| 7,637,950 B2 | 12/2009 | Baccelli et al. |
| 7,727,246 B2 | 6/2010 | Sixta et al. |
| 7,862,616 B2 | 1/2011 | Lechmann et al. |
| 8,034,060 B2 | 10/2011 | Keren et al. |
| 8,328,872 B2 | 12/2012 | Duffield et al. |
| 8,403,986 B2 | 3/2013 | Michelson |
| 8,747,444 B2 | 6/2014 | Moskowitz |
| 8,920,438 B2 | 12/2014 | Aranyi |
| 9,744,049 B2* | 8/2017 | Kueenzi ............... A61F 2/4455 |
| 2002/0068977 A1 | 6/2002 | Jackson |
| 2002/0143338 A1 | 10/2002 | Orbay et al. |
| 2004/0088054 A1 | 5/2004 | Berry |
| 2004/0177531 A1 | 9/2004 | DiBenedetto et al. |
| 2004/0254644 A1 | 12/2004 | Taylor |
| 2005/0010290 A1 | 1/2005 | Hawkins |
| 2005/0027362 A1* | 2/2005 | Williams ................ A61F 2/442 623/17.11 |
| 2005/0049590 A1* | 3/2005 | Alleyne ................. A61F 2/442 623/17.11 |
| 2005/0177235 A1 | 8/2005 | Baynham et al. |
| 2005/0216084 A1 | 9/2005 | Fleischmann |
| 2005/0273170 A1 | 12/2005 | Navarro et al. |
| 2005/0278026 A1 | 12/2005 | Gordon et al. |
| 2007/0213820 A1 | 9/2007 | Magerl et al. |
| 2009/0105831 A1 | 4/2009 | Jones et al. |
| 2010/0145460 A1 | 6/2010 | McDonough et al. |

OTHER PUBLICATIONS

E.K. Wai et al., "Disk Replacement Arthroplasties: Can The Success of Hip and Knee Replacements be Repeated in the Spine?," Seminars in Spine Surgery, vol. 15, No. 4 Dec. 2003, pp. 473-482.
Richard D. Guyer et al., "Intervertebral Disc Prostheses," Spine Journal, vol. 28, No. 15S, Supp. To Aug. 1, 2003, pp. S15-S23.
Dieter Grob et al., "Clinical Experience With the Dynesys Semirigid Fixation System for the Lumbar Spine," Spine, vol. 30, No. 3, 2005, pp. 324-331.
International Search Report (ISR) and Written Opinion of the International Searching Authority, Dec. 3, 2007, International Application No. PCT/US 07/05005.

(56) References Cited

OTHER PUBLICATIONS

International Search Report (ISR) and Written Opinion of the International Searching Authority, May 21, 2008, International Application No. PCT/US2007/021015.
International Search Report (ISR) and Written Opinion of the International Searching Authority, Jul. 9, 2008, International Application No. PCT/US2007021013.

* cited by examiner

BIDIRECTIONAL FIXATING INTERVERTEBRAL IMPLANT SYSTEM

The present Application is a Continuation of U.S. application Ser. No. 14/299,711 filed Jun. 9, 2014, which is a Continuation Application of U.S. patent application Ser. No. 12/868,451 filed Aug. 25, 2010, now U.S. Pat. No. 8,747,444 issued Jun. 10, 2014, which is a Divisional Application of U.S. patent application Ser. No. 11/536,815 filed on Sep. 29, 2006, now U.S. Pat. No. 7,846,188 issued Dec. 7, 2010, which is a Continuation-In-Part Application of U.S. patent application Ser. No. 11/208,644, filed on Aug. 23, 2005, now U.S. Pat. No. 7,704,279 issued on Apr. 27, 2010, which claims priority to U.S. Provisional Application No. 60/670,231, filed on Apr. 12, 2005; the entire contents of all the above identified patent applications are hereby incorporated by reference.

FIELD OF INVENTION

The present invention relates to a unique universal bidirectional screw (UBS) system, and in particular its application to the spine, also referred to as bi-directional fixating transvertebral (BDFT) screws which can be used to supplement other intervertebral spacers and/or bone fusion materials. BDFT screws can be incorporated into anterior and/or posterior cervical, thoracic and lumbosacral, novel, zero-profile, horizontal intervertebral mini-plates, and anterior cervical, thoracic and lumbosacral total interbody fusion devices (IBFD). In the lumbosacral and thoracic spine, BDFT screws can be used independently or supplemented with the horizontal intervertebral mini-plate or total IBFD, and are thus considered stand alone intervertebral body fusion constructs which may obviate the need for supplemental pedicle screw fixation. In the cervical spine these devices obviate the need for supplemental vertically oriented anterior plating, and can be used as stand alone interbody fusion devices. The present invention also relates to a stand-alone or supplemental, calibrating interarticular joint stapling device which can incrementally fine-tune posterior interarticular joint motion.

DESCRIPTION OF THE RELEVANT ART

Segmental spinal fusions which stabilize two or more adjacent segments of the spine are performed for painful degenerative disc disease, recurrent disc herniations, spinal stenosis, spondylolysis and spondylolisthesis. Over the past several decades a wide variety of fusion techniques and instrumentation have evolved. One of the earliest posterior fusion techniques entails non-instrumented in-situ on-lay posteriolateral fusion utilizing autologous iliac crest bone. Because of the high rate of imperfect fusions i.e. pseudoarthroses, transpedicular pedicle screw fixation which utilizes a variety of rods and interconnectors were developed to achieve less interbody motion and hence higher fusion rates. Pedicle screw fixation was initially combined with on-lay posteriolateral fusion. Because of the poor blood supply of the transverse processes, issues still remained with pseudoarthroses. In an attempt to address this problem, pedicle screw fixation has been supplemented with a variety of interbody fusion devices. This is based on the concept that axial loading enhances fusion and that the vertebral endplates have a better blood supply. Interbody lumbar fusion devices can be placed anteriorly via an anterior lumbar interbody fusion technique (ALIF) or posteriorly via a posterior lumbar interbody fusion technique (PLIF). Material options for interbody fusion devices have included autologous iliac crest/laminar bone, cylindrical threaded titanium interbody cages, cylindrical threaded cortical bone dowels, vertebral interbody rings or boxes, carbon fiber cages, or femoral ring allograft. To lessen the complication of prolonged nerve root retraction the technique of circumferential transforaminal lumbar interbody fusion technique (TLIF) has been introduced. This employs the transforaminal placement of an interbody spacer such as one kidney bean shaped allograft, two circular allografts, one or two titanium circular cages, a single titanium or Peek (polyether-ketone) boomerang spacer. The threaded spacers are usually supplemented with autologous bone and/or bone morphogenic protein (BMP), demineralized bone matrix (DBM) in the form of paste or cement, rh-BMP with collagen sponges, or similar osteoinductive biological agents which are known to enhance fusion.

Currently all lumbosacral fusion techniques, ALIF, PLIF and TLIF, are typically supplemented by pedicle screw placement. In addition posterior transfacet screws also have been used to supplement ALIF procedures. Complications of pedicle screw placement include duration of procedure, significant tissue dissection and muscle retraction, misplaced screws with neural and/or vascular injury, excessive blood loss, need for transfusions, prolonged recovery, incomplete return to work, excess rigidity leading to adjacent segmental disease requiring further fusions and re-operations. Further advances of pedicle screw fixation including minimally invasive and image-guided technology, and the development of flexible rods have imperfectly addressed some but not all of these issues. Transfacet screws and similar embodiments entail the use of short or long screws which provide static facet alignment without motion calibration.

Complications of all current interbody fusion devices is their lack of coverage of the majority of the cross sectional area of the vertebral endplates and their potential for extrusion. The recently described flexible fusion system which consists of flexible rods attached to transpedicular screws (Dionysis, Zimmer) suffers from a high pull-out rate, higher rate of re-operation than standard fusions, and does not rank high with patient satisfaction. See for example, *Clinical experience with the Dynesys semirigid fixation system for the lumbar spine: Surgical and patient-oriented outcome in 50 cases after an average of 2 years*; D, Grob, A. Benini and A. F. Mannion. Spine Volume 30, number 3, Feb. 1, 2005.

Single or multiple level anterior cervical spinal fusions typically employ the replacement of the cervical disc or discs with autologous or allograft bone, or an intervertebral spacer filled with autologous or allograft bone, demineralized bone matrix, BMP or rh-BMP etc. Currently these anterior cervical fusions are augmented with anterior vertical titanium plates which cross the intervertebral space or spaces and are secured to the vertebral bodies above and below the disc space or spaces with perpendicularly penetrating vertebral body screws. The purpose of these plates is to serve as a barrier to prevent extrusion of the intervertebral disc replacement. Recently anterior vertical plating has also been employed in anterior lumbar fusion.

Complications of anterior spinal plating include the potential for neurovascular injury with screw misplacement, screw and/or plate pull-out, and screw and/or plate breakage. Other complications include potential esophageal compression/injury in the cervical spine secondary to high plate profile or pull-out, and to potential devastating vascular injury in the lumbar spine with plate movement and/or dislodgement into anterior iliac vasculature. Recent advances in cervical plating have therefore concentrated on the creation of lower profile plates and even resorbable plates. These advances, however, have not eliminated the possibility of plate dislodgement and screw back out/breakage.

OBJECTS OF THE INVENTION

To achieve segmental fusion, applicants propose the use of novel bi-directional fixating transvertebral (BDFT) screws which can be strategically inserted via anterior or posterior surgical spinal approaches into the anterior and middle columns of the intervertebral disc space. The BDFT mechanism employs turning a wormed driving screw which then turns a spur gear which in turn simultaneously turns a rostrally oriented screw into the cephalad vertebral body, and a caudally directed screw into the caudal vertebral body. The vertebral bodies above and below the disc space by virtue of their engagement and penetration by the BDFT screws are thus linked and eventually fused. The gear box casings of the BDFT screws prevent vertebral body subsidence. The inside of the denuded intervertebral space can then be packed with autologous or allograft bone, BMP, DBX or similar osteoinductive material. Posteriorly or anteriorly in the lumbar spine, these screws can be capped with a horizontal mini-plate which will prevent bony growth into the thecal sac and nerves. We refer to this as a two-in-one design i.e. two BDFT screws combined with one horizontal mini-plate. Anteriorly a total intervertebral spacer containing three BDFT screws can be inserted. We refer to this as a three-in-one design i.e. three BDFT screws in one total fusion construct, i.e. an IBFD.

Applicants postulate that BDFT screws provide as strong or stronger segmental fusion as pedicle screws without the complications arising from pedicle screw placement which include screw misplacement with potential nerve and/or vascular injury, violation of some healthy facets, possible pedicle destruction and blood loss. By placing screws across the intervertebral space from vertebral body to vertebral body engaging anterior and middle spinal columns, and not into the vertebral bodies via the transpedicular route, some of the healthy facet joints are preserved. Because this technique accomplishes both anterior and middle column fusion, without rigidly fixing the posterior column, it in essence creates a flexible fusion. This device therefore is a flexible fusion device because the preserved posterior joints retain their function achieving at least a modicum of mobility and hence a less rigid (i.e. a flexible) fusion.

The very advantage of trans-pedicular screws which facilitate a strong solid fusion by rigidly engaging all three spinal columns (anterior, middle and posterior), is the same mechanical mechanism whereby complete inflexibility of all columns is incurred thereby leading to increasing rostral and caudal segmental stress which leads to an increased rate of re-operation.

Transvertebral fusion also leads to far less muscle retraction, blood loss, and significant reduction in O.R. time. Thus the complication of pedicular screw pull-out and hence high re-operation rate associated with the current embodiment of flexible fusion pedicle screws/rods is obviated. The lumbosacral BDFT screws can be introduced via PLIF, TLIF or ALIF operative techniques. Although one can opt to supplement these screws with transpedicular screws there would be no absolute need for supplemental pedicle screw fixation with these operative techniques.

Bi-directional fixating transvertebral (BDFT) screws can also be combined with novel zero-profile horizontal cervical and lumbar mini-plates. They can also be combined with a total IBFD with insertion spaces for bone material insertion.

For the performance of anterior cervical, and lumbar anterior or posterior fusions one or two centrally placed BDFT screws anterior to an interverterbal graft or spacer, may be a sufficient barrier by itself to prevent device/graft extrusion. However, to further safeguard against graft/spacer extrusion, applicants have devised horizontal linear mini-plates which can be incorporated into two anteriorly placed BDFT screws. It can also be incorporated into two posteriorly BDFT screws which are inserted posteriorly, in addition to a third BDFT screw which has been inserted centrally and posteriorly. This achieves a total disc intervertebral construct placed posteriorly composed of three BDFT screws placed in a triangulating matter. The capping horizontal mini-plate would prevent the bony material which is packed into the interspace from growing into the ventral; aspect of the nerves. The horizontal linear mini-plates traverse the diameter of the disc space and most of the disc space height. Thus a horizontal mini-plate placed posteriorly immediately beneath the lumbosacral thecal sac and nerve roots which is capped and secured to right and left BDFT screws, would prevent intervertebral device/graft extrusion. This mini-plate is essentially a zero-to sub-zero-profile plate in that it is either flush with or below the rostral and caudal vertebral body surfaces.

Because the BDFT screws engage a small percentage of the rostral and caudal vertebral body surface area, this plating system could be performed at multiple levels. This plating system which utilizes BDFT screws in the anterior cervical spine does not lead to any esophageal compression/injury, or vascular iliac vein injury in the lumbar spine. For the performance of two or three level intervertebral fusion with horizontal mini-plates there is virtually no possibility of plate breakage which can occur in long vertical anterior plates which are in current usage. Similarly, screw dislodgement, if it occurs would lead to minimal esophageal compression or injury compared to large vertical plate/screw dislodgement. In addition, in the cervical spine BDFT screw placement closer to the midline would avert any possibility of lateral neural or vertebral artery injury. Likewise multiple placement of IBFD devices can also be performed without the above mentioned risks and complications.

If one were inclined to further enhance posterior column thoraco-lumbosacral fixation, applicants introduce a novel calibrated facet stapling device which staples the inferior articulating facet of the superior segment to the superior articulating facet of the caudal vertebral segment unilaterally or bilaterally, further minimizing motion until interbody fusion occurs. The degree of flexibility can be further modulated by varying the calibration strength and torque of facet stapling. This would be dictated by the need for greater or lesser degrees of motion preservation. All other know transfacet stabilizers are not calibrated, but are static.

Currently, failed anterior lumbar arthoplasties are salvaged by combined anterior and posterior fusions. BDFT screws and/or IBFDs could be utilized as a one-step salvage operation for failed/extruded anteriorly placed lumbar artificial discs obviating the above salvage procedures which have greater morbidity. Likewise, for anterior cervical fusion, applying cervical BDFT screws alone or in combination with cervical mini-plates or IBFDs addresses the deficiencies and complications of current cervical plating technology as mentioned above.

BRIEF DESCRIPTION OF THE DRAWINGS

FIG. 12A illustrates the drive rod. FIG. 12B illustrates the fulcrum cylinder connector. FIG. 12C illustrates the grip handle. FIG. 12D illustrates the cylinder. FIG. 12E illustrates the cylinder with the drive rod.

DETAILED DESCRIPTION OF THE INVENTION

1. The Medical Device

Referring to FIGS. 1A-5C the above described problem can be solved in the cervical, thoracic and lumbar spine by insertion into the denuded intervertebral disc space a bi-directional fixating transvertebral (BDFT) screw or (UBS) screws 100.

Figure 1A:
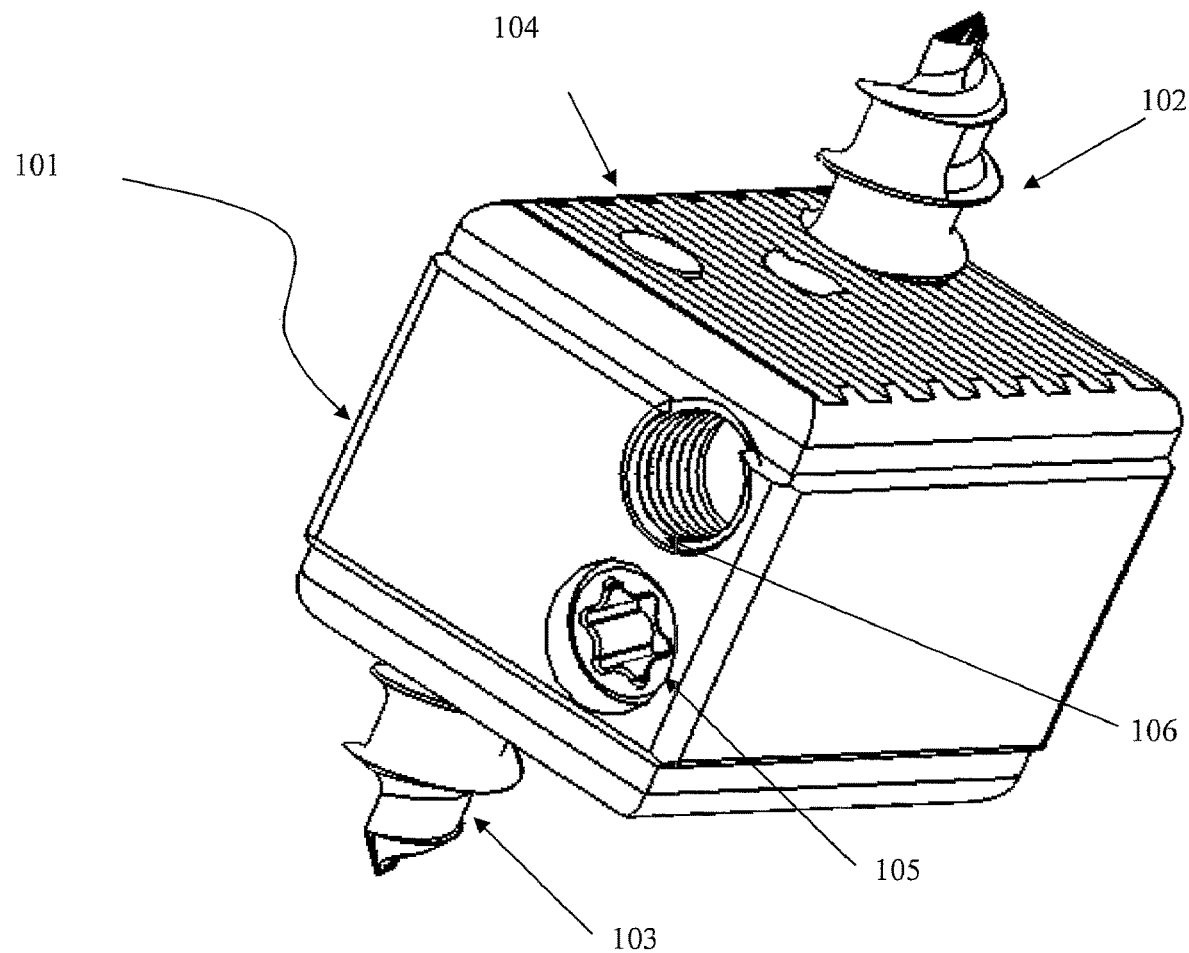
FIG. 1A illustrates an isometric view of the universal bidirectional screw (UBS) alternatively referred to as the bi-directional fixating transvertebral screw (BDFT).
Figure 1B:
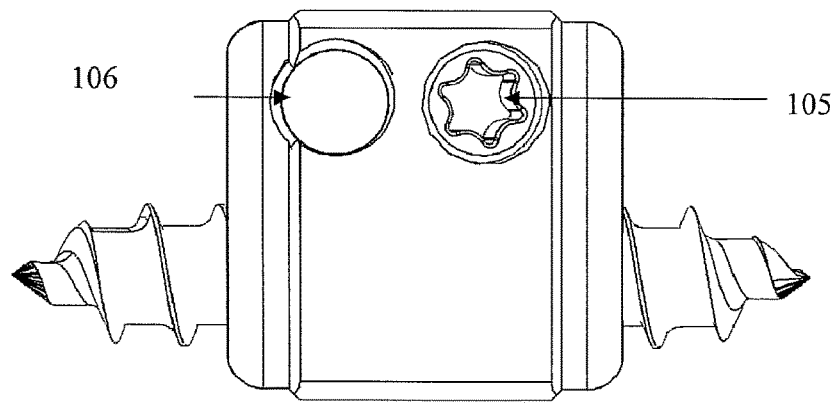
FIG. 1B illustrates the lateral view of the UBS (BDFT) with rostral and caudal screws partially extended.
Figure 1C:
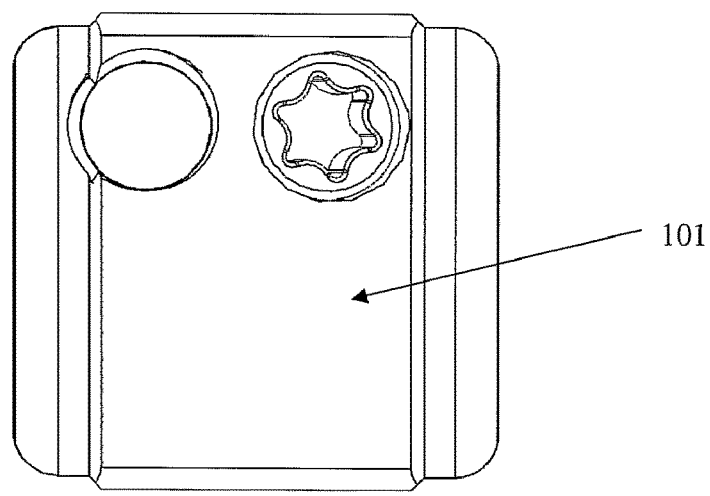
FIG. 1C illustrates the lateral view of the UBS (BDFT) with the screws withdrawn.
Figure 2:
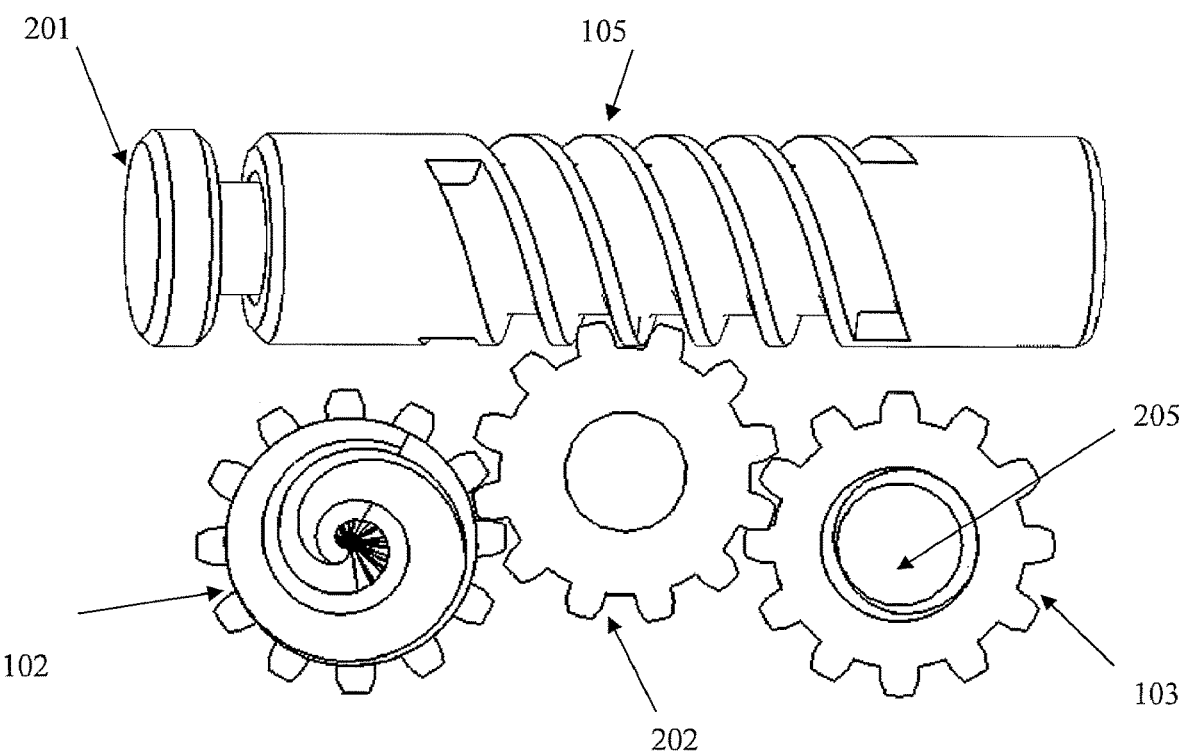
FIG. 2 illustrates a front view of the UBS (BDFT) without the gear box and cover.
Figure 3A:
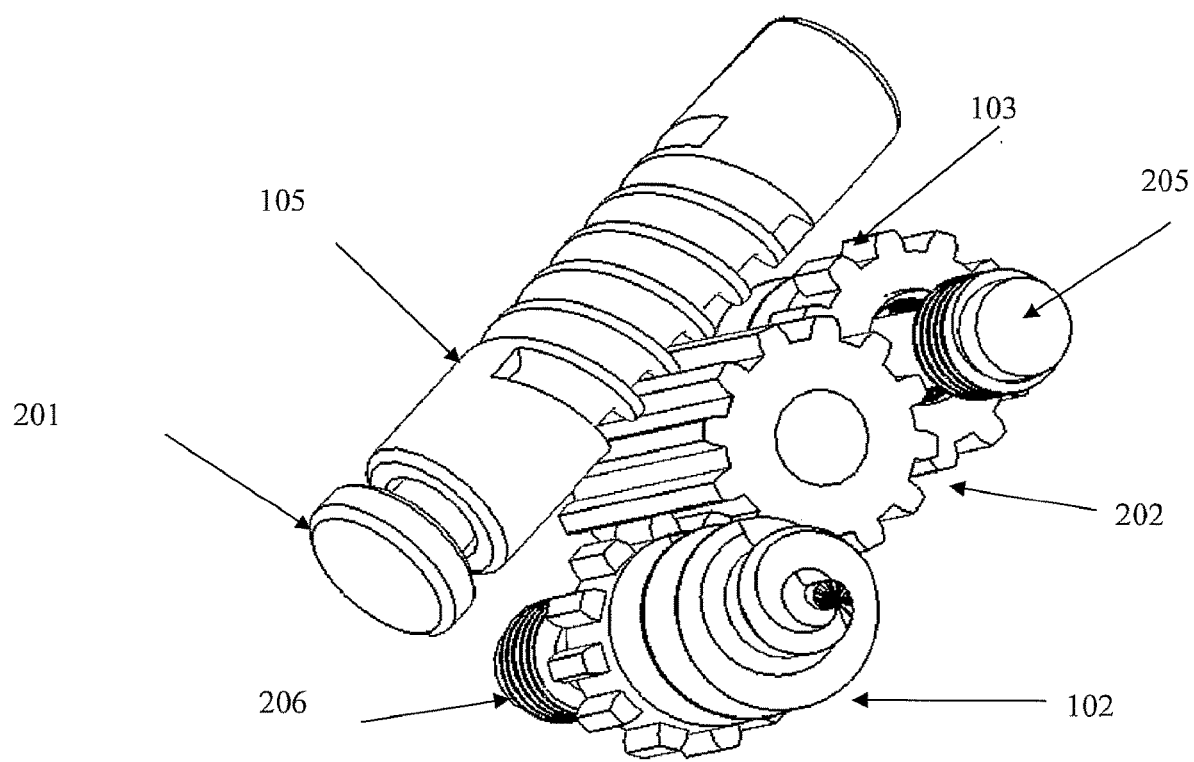
FIG. 3A and 3B illustrate perspective, and exploded perspective views, respectively, of the UBS (BDFT) without gear box and cover, with the screws fully extended.
Figure 3B:
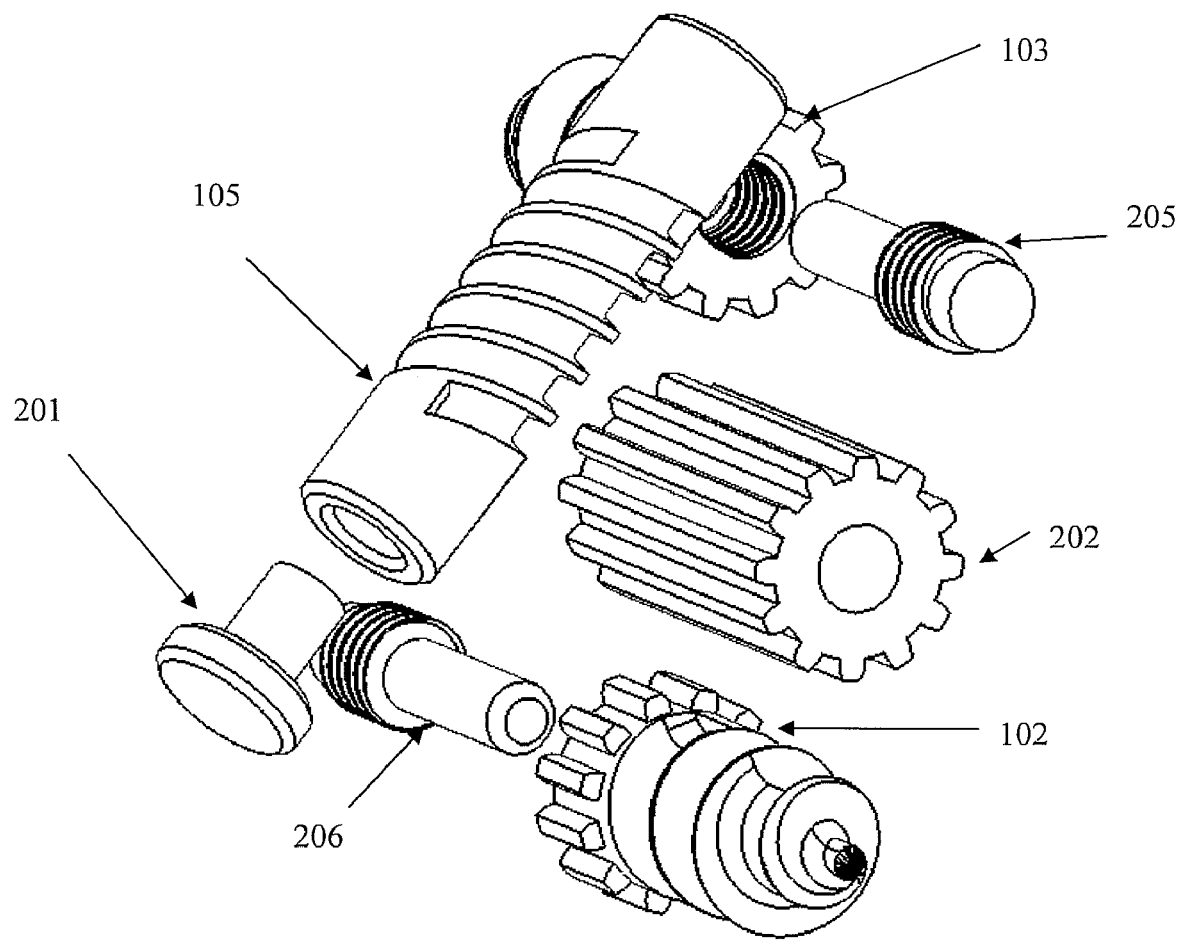
Figure 4:
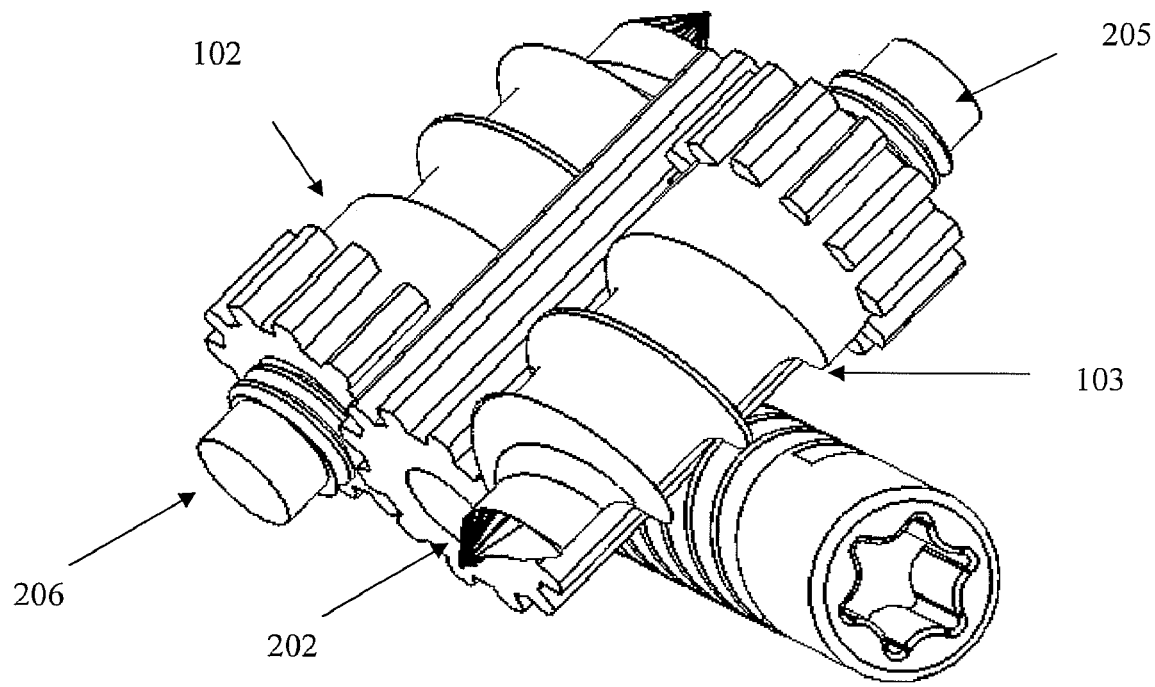
FIG. 4 illustrates a perspective view of the UBS (BDFT) without the gear box and cover, with screws partially extended.

FIGS. 1A through 1C illustrate three-dimensional views of the UBS/BDFT screw 100. All its inner components are in the gear box casing 101. The internal mechanisms are illustrated in FIGS. 2-5C. FIG. 1A illustrates the isometric view of the UBS 100 showing the outer gear box 101 containing the external mechanism, with superior screw 102 and inferior screw 103 extended. There are serrations 104 on the superior and inferior surfaces of the box 101 intended to integrate with the surface of the superior and inferior vertebral body surfaces. The gear box 101 which is made either of PEEK (polyethylene-ketol) or titanium acts as a column preventing subsidence of the disc space. Also seen are the surface of the worm drive screw 105, and the horizontal mini-plate screw insert 106 for capping the horizontal mini-plate to the gear box's 101 surface (FIGS. IA-C and 6A-C).

FIGS. 1-4 illustrate the inner components of the BDFT/UBS 100 without the enclosing gear box 101. The inner components include a single wormed drive screw 105, a drive spindle 201, a spur gear 202, superior screw 102 and inferior screw 103 with superior and inferior screw spindles 205, 206 (FIGS. 1-4). The mechanism of operation is thus: The wormed drive screw 105 is rotated clockwise. This rotation in turn rotates the spur gear 202. The spur gear 202 interdigitates with the superior screw 102 on one side and the inferior screw 103 on the other side. Rotation of the spur gear 202 leads to simultaneous rotation of the superior and inferior screws 102, 103 in equal and opposite directions. The spindles in the wormed drive screw 105 and the superior and inferior screws 102, 103 maintain the axis of screw orientation. The screws 102, 103 are self drilling and hence there is no need for bony preparation.

Figure 5A:
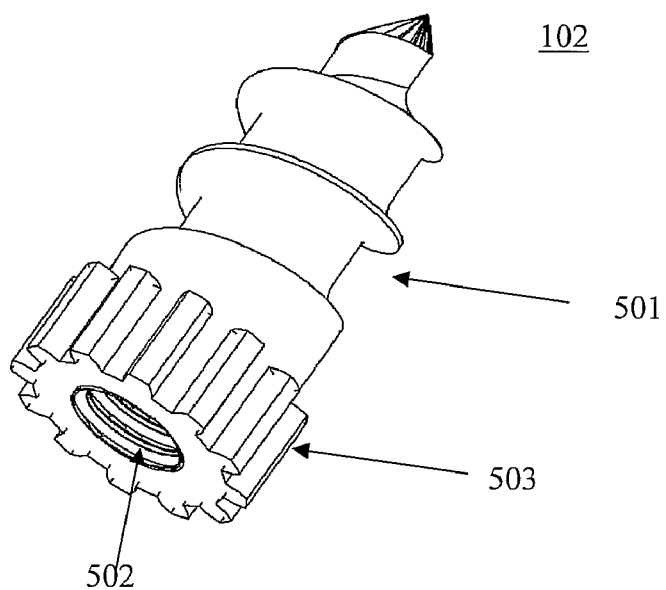
FIG. 5A illustrates a perspective view of a single insertion screw of the BDFT.
Figure 5B:
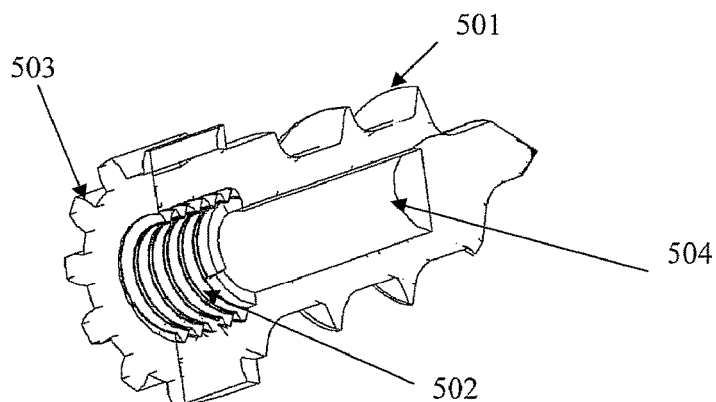
FIG. 5B illustrates a perspective cross-sectional view of a BDFT insertion screw.

FIGS. 5A and 5B illustrate in perspective and cross-sectional views the detailed elements of the superior and inferior screws 102, 103. These figures illustrate the external threading 501, the internal threading 502, the spindle socket and the spur gear teeth 503 which interdigitate with the spur gear 202. The screws 102, 103 are self drilling as noted.

Figure 5C:
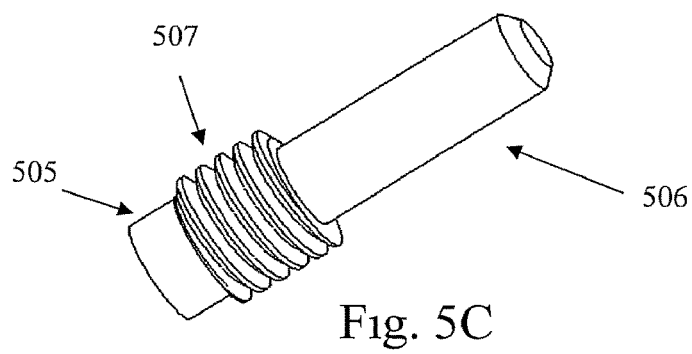
FIG. 5C illustrates a perspective view of the spindle.

FIG. 5C illustrates the details of the spindle including its base 505, its rod 506 and its threaded segment 507.

Figure 6A:
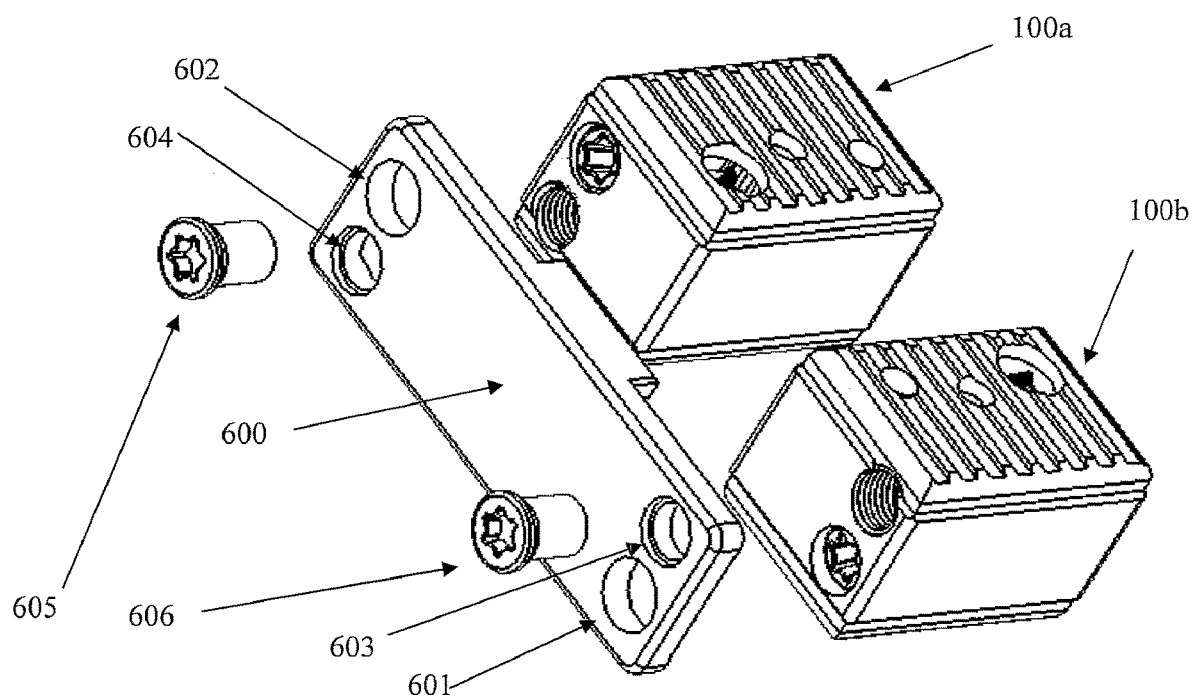
FIG. 6A illustrates an exploded view of the two-in-one design consisting of two BDFT screws and a horizontal mini-plate.
Figure 6B:
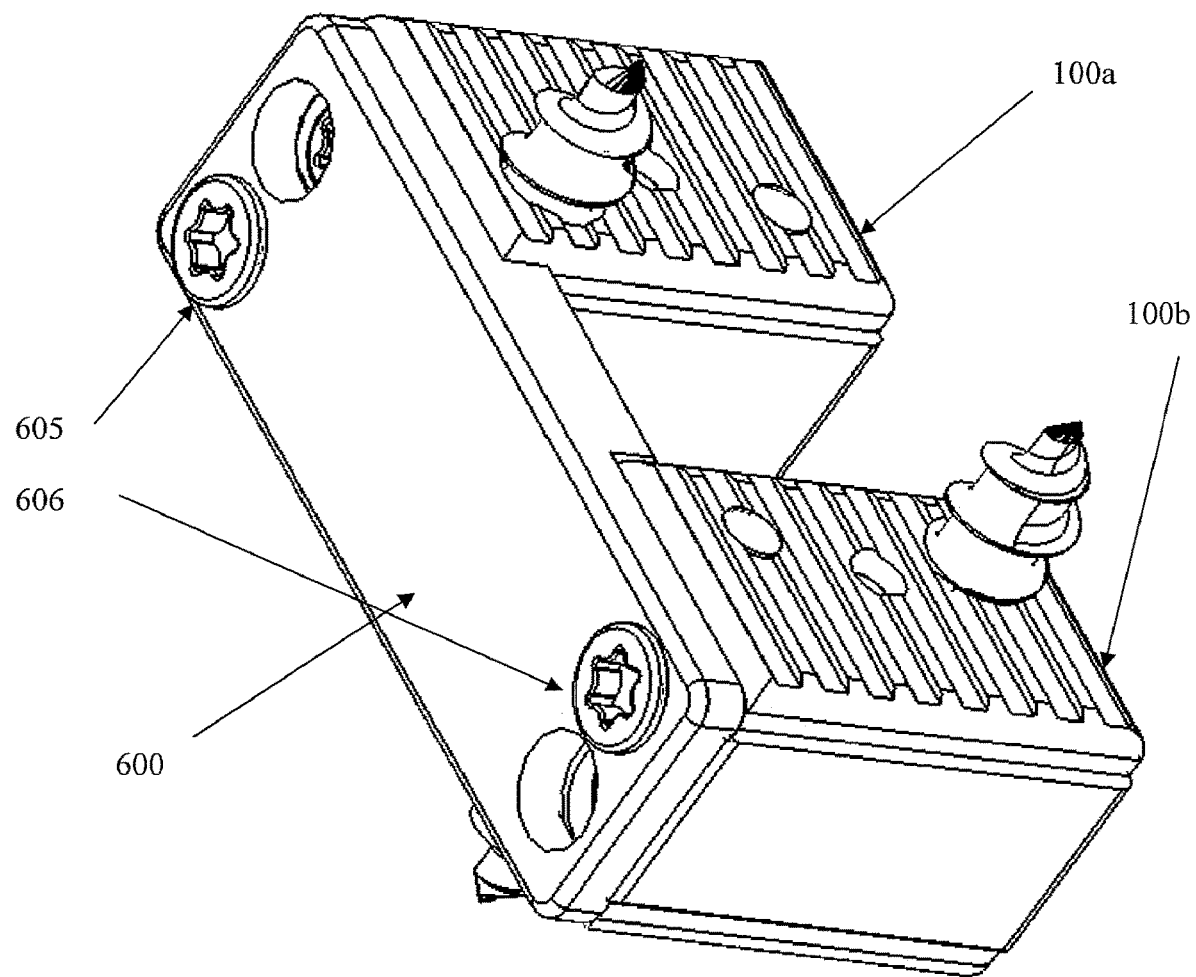
FIG. 6B illustrates the two-in-one design with the horizontal mini-plate secured and the screws extended.
Figure 6C:
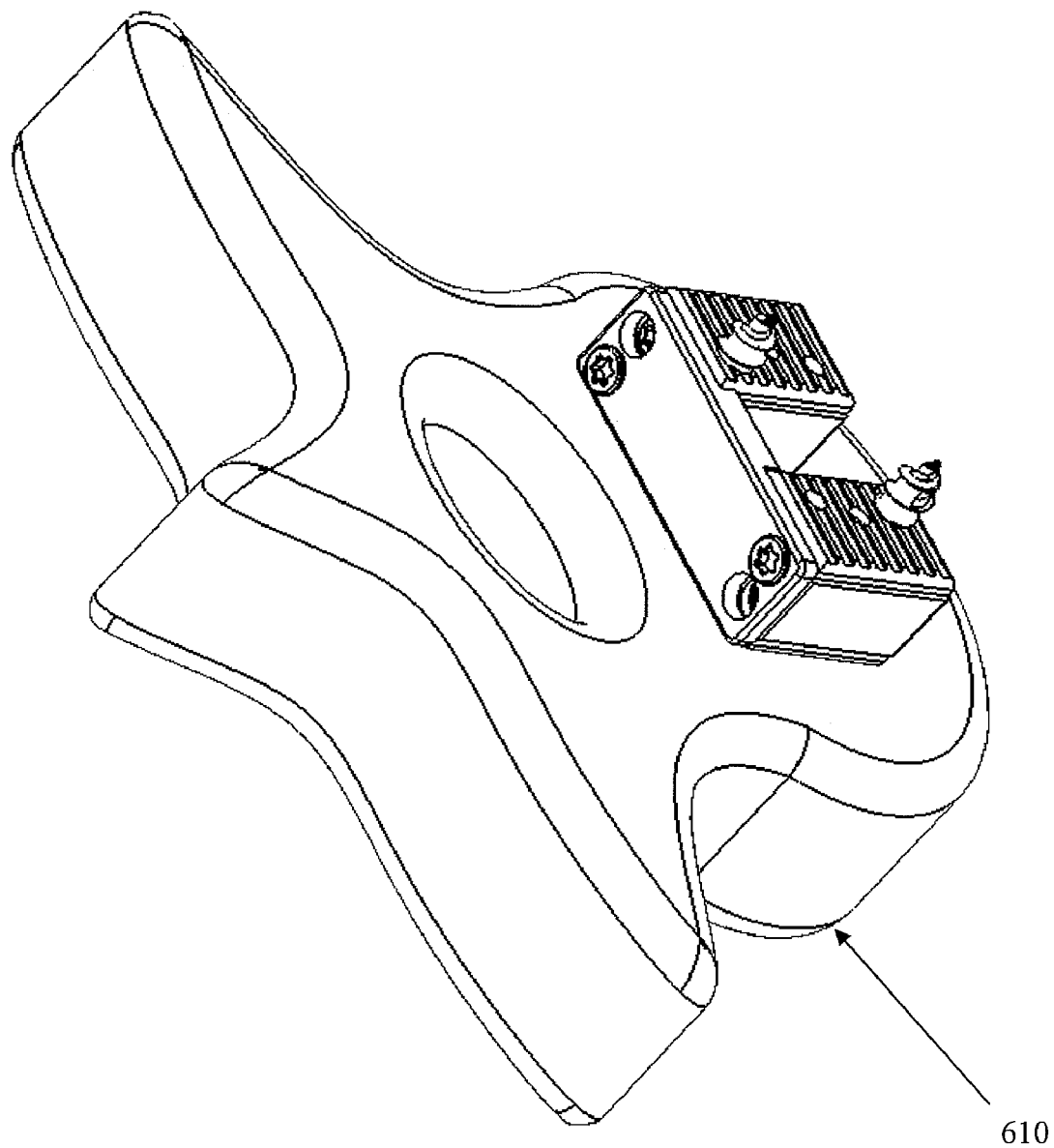
FIG. 6C illustrates the two-in-one design, and its position with respect to the vertebral body.

FIGS. 6A-6C illustrate the two-in-one design concept. This design concept includes two UBS/BDFT screws 100a, 100b which are placed in the left and right portions of the intervertebral disc space, which are then capped by a horizontal mini-plate 600. Note how the mini-plate has four perforations. There are two perforations 601, 602, one on each side to allow entry of the wormed screw drive into the gear box. There are an additional two perforations 603, 604, one on each side, to secure the plate to the two UBS boxes 100a, 100b with plate screw caps 605, 606. FIG. 6C demonstrates the position of the two-in-one system with respect to the vertebral body 610. In between the two BDFT/UBS screws 100a, 100b, bone fusion material is inserted. The horizontal mini-plate 600 prevents the bone from growing into the nerves above it. With this system it is also possible to place a third screw inferior and in the middle of the two other UBS screws 100a, 100b thereby providing additional screw intervertebaral fixation.

Figure 7A:
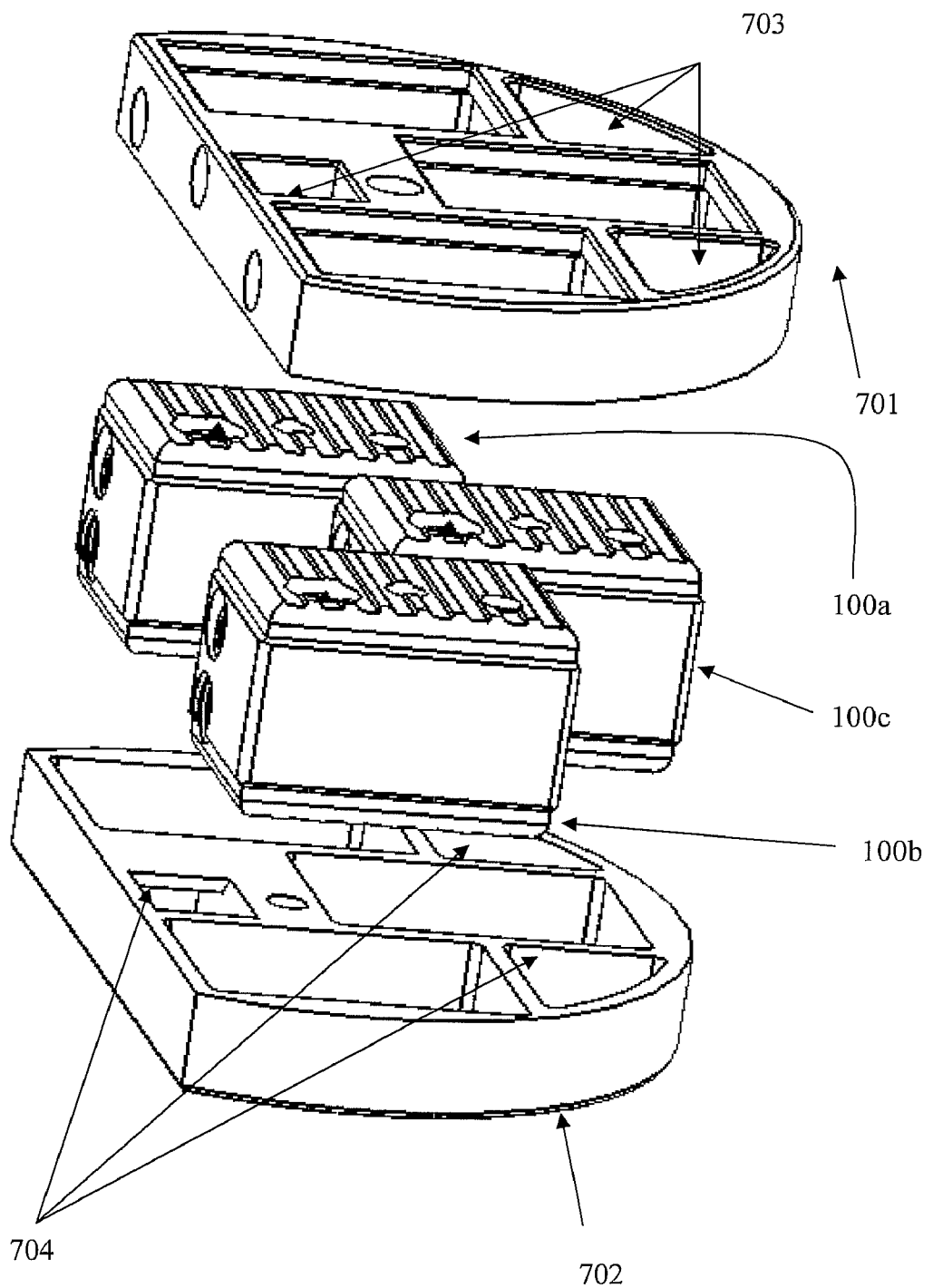
FIG. 7A illustrates an exploded view of the three-in-one system (IBFD) which consists of three BDFT screws in an enclosure system.
Figure 7B:
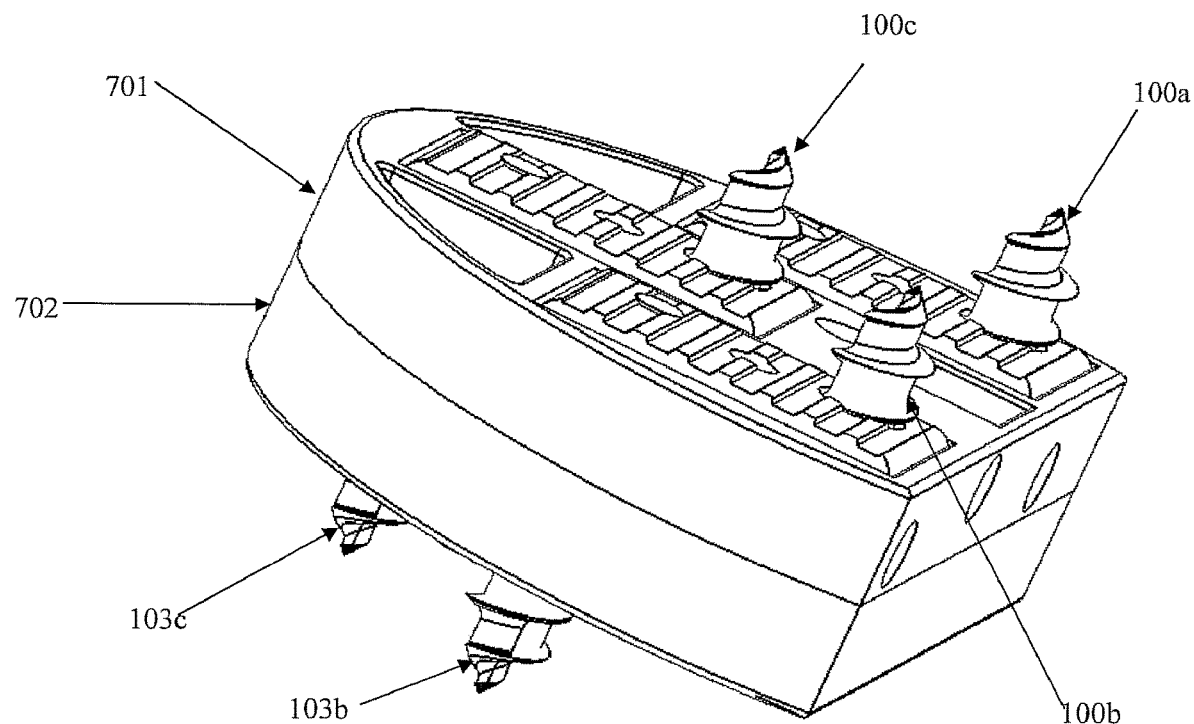
FIG. 7B illustrates the three-in-one system (IBFD) with screws extended.
Figure 7C:
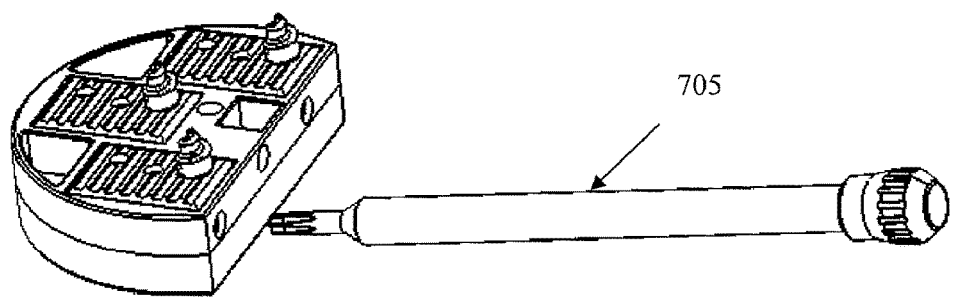
FIG. 7C illustrates the IBFD with an accompanying screw driver.

FIGS. 7A through 7C illustrate the three-in-one design otherwise known as the IBFD. This device consists of five components. Three UBS/BDFT screws 100a, 100b, 100c, a superior and an inferior enclosure 701, 702. The enclosures 701, 702 are attached to the UBS/BDFT screws 100a, 100b, 100c. A screw driver 705 is used to actuate the screws 100a, 100b, 100c. There are also slots 703, 704 for bone fusion material. This device is only for anterior insertion into the spine, and it covers the entire cross-sectional area of the interspace, and is thus a total IBFD. The enclosures can be made out of PEEK, titanium, cobalt chromium or any other similar substance. The structure of the device provides significant three column stability and prevents subsidence of the construct.

Figure 8A:
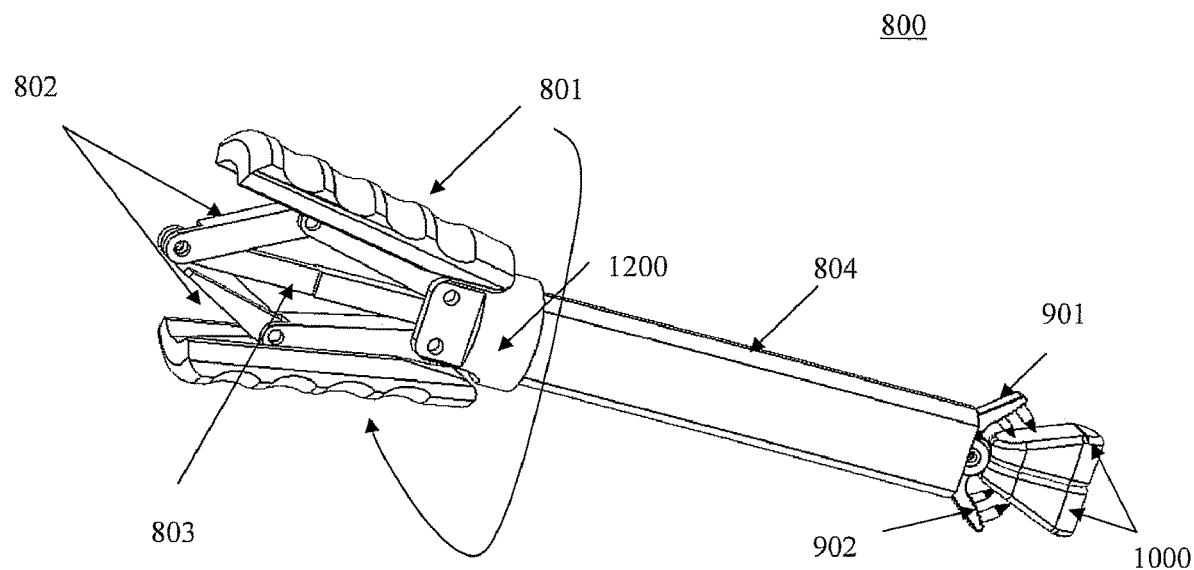
FIGS. 8A and 8B illustrate perspective, and cross-sectional views of the interarticular joint stapling device with staple, respectively.
Figure 8B:
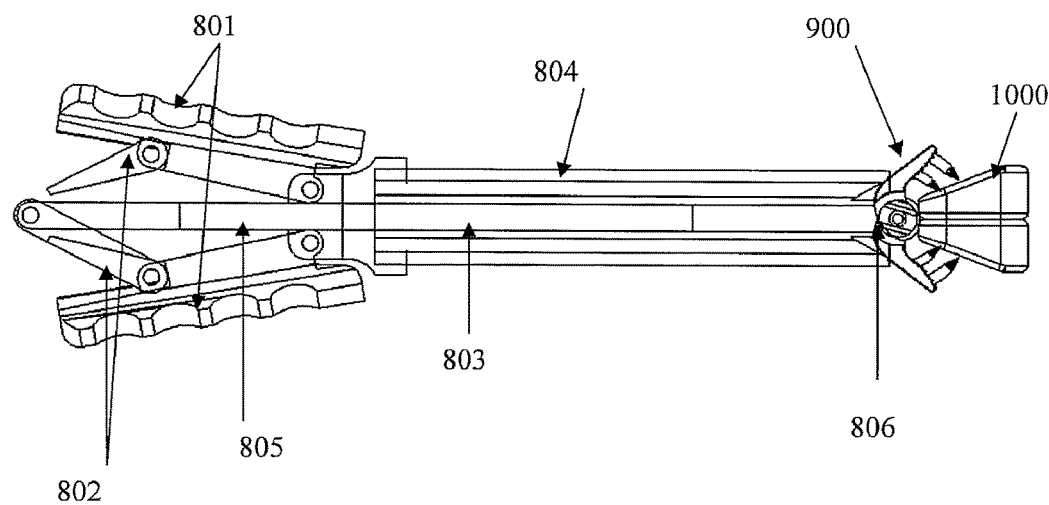

FIG. 8A and 8B illustrate the individual components of the facet joint staple gun 800. It consists of a remote action mechanism which includes grip handles 801, transmission linkages 802, a drive rod 803, a cylinder 804. The drive rod 803 has a force end 805 and an action end 806.

Figure 9A:
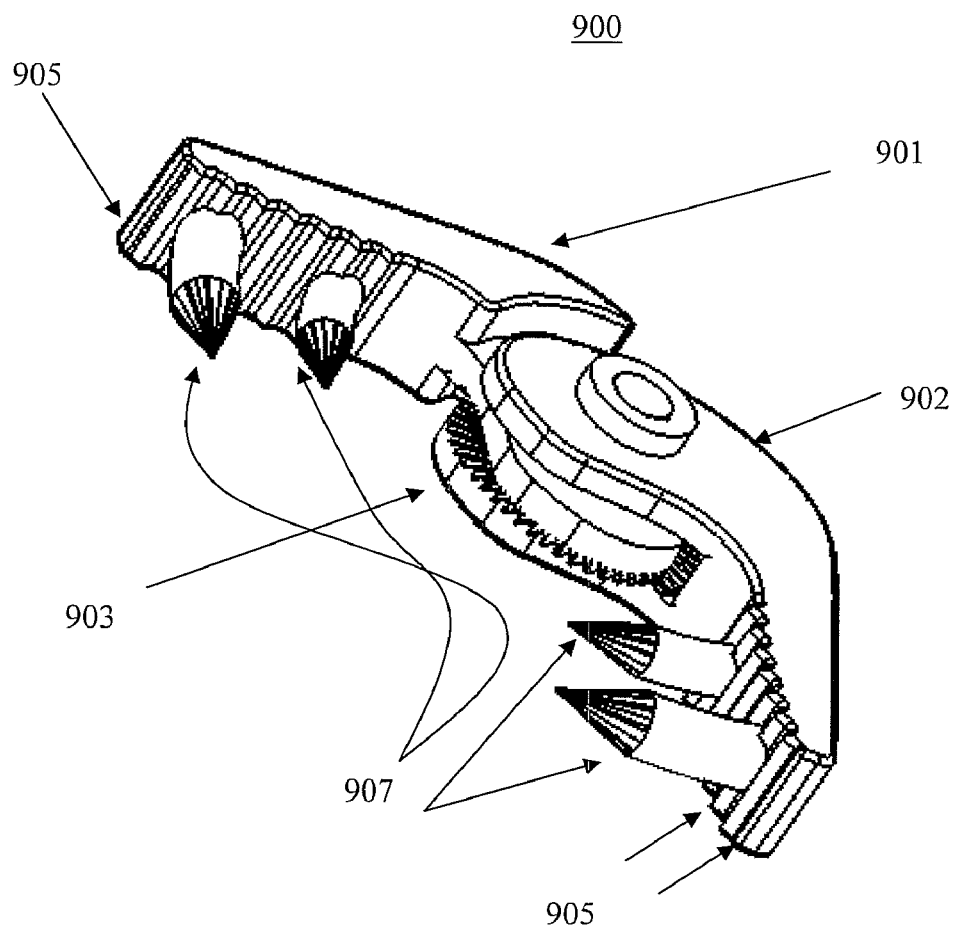
FIGS. 9A and 9B illustrate perspective and exploded views of the staple, respectively.
Figure 9B:
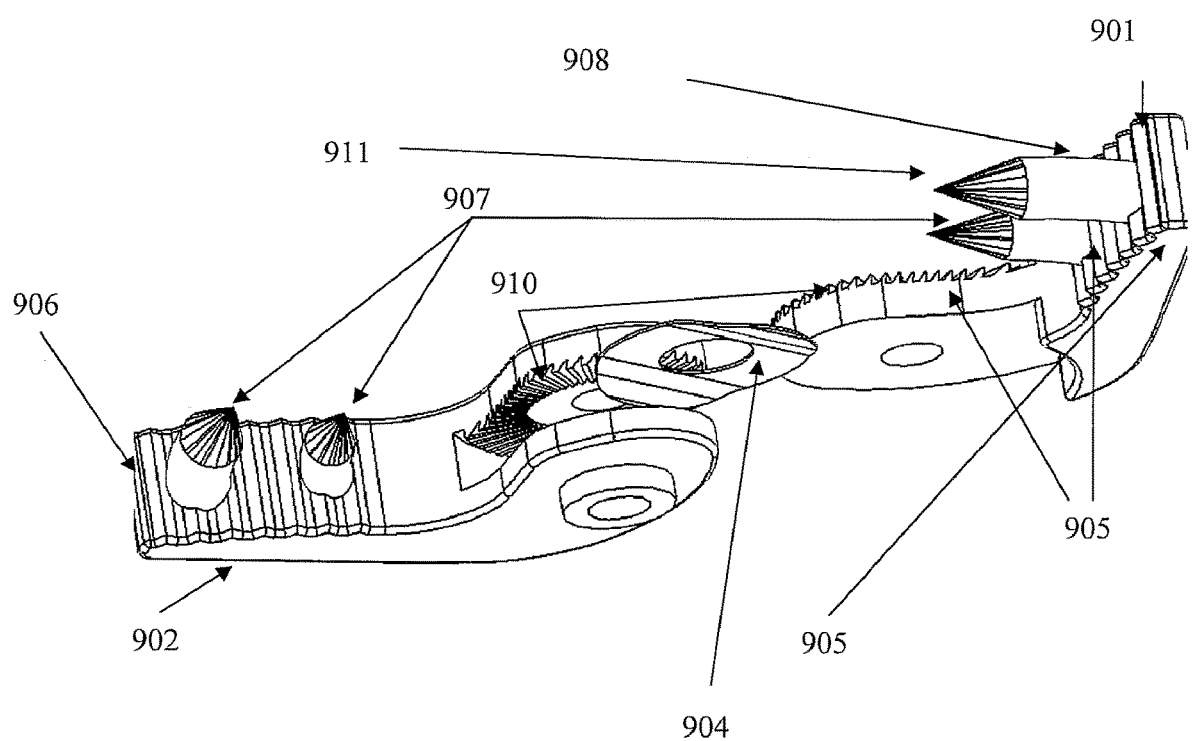
Figure 10:
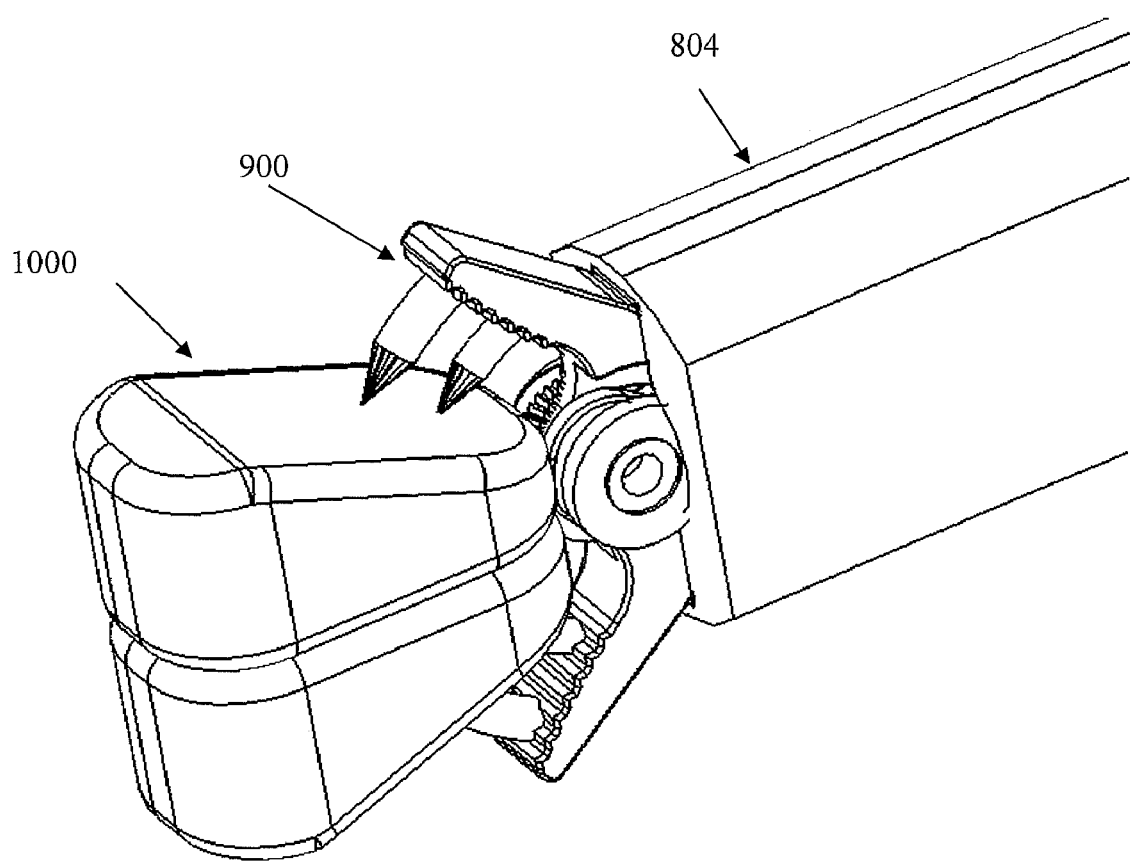
FIG. 10 illustrates a perspective view of the staple gun engaging the facet joint.

FIGS. 9A and 9B illustrate the details of the facet joint stapler. The staple 900 has superior and inferior staple segments 901, 902. These segments 901, 902 are joined by a teethed unidirectional locking mechanism 903 having right triangular teeth 910, and a spring washer 904. The inferior surfaces 905, 906 of each staple segment 901, 902 are serrated to facilitate bony integration, and each segment has two bone piercing elements 907 with a base 908. FIG. 10 illustrates the staple 900 in the staple gun 800, in the opened position engaging the facet joints, prior to penetration and stapling.

Figure 11:
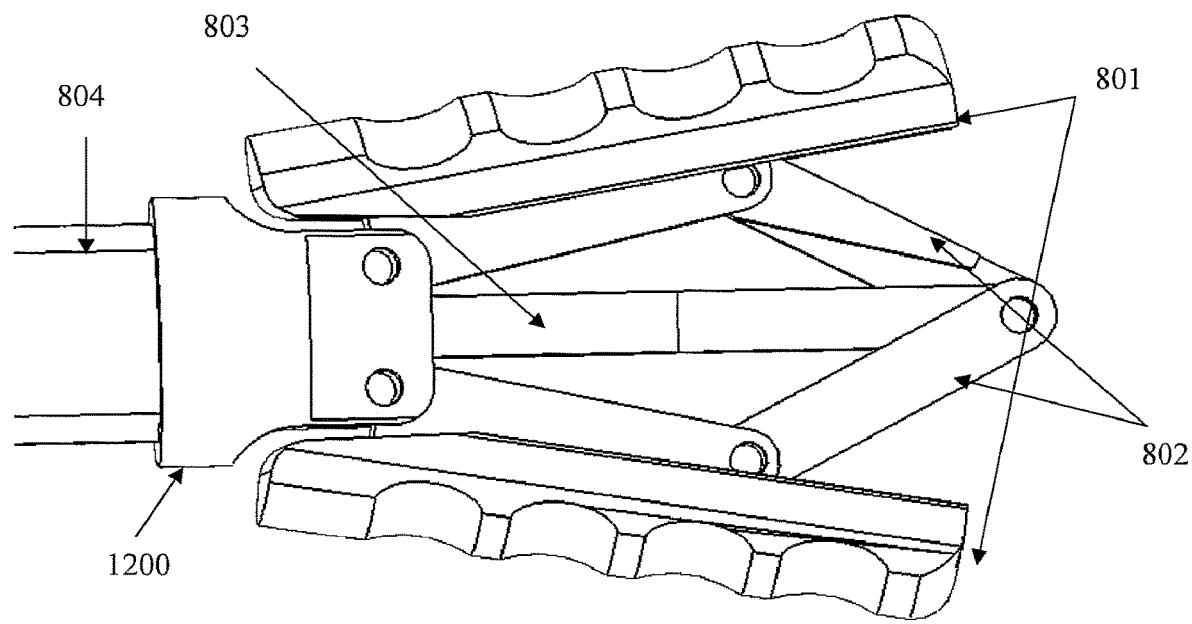
FIG. 11 illustrates the remote action mechanism of the staple gun.
Figure 12A:
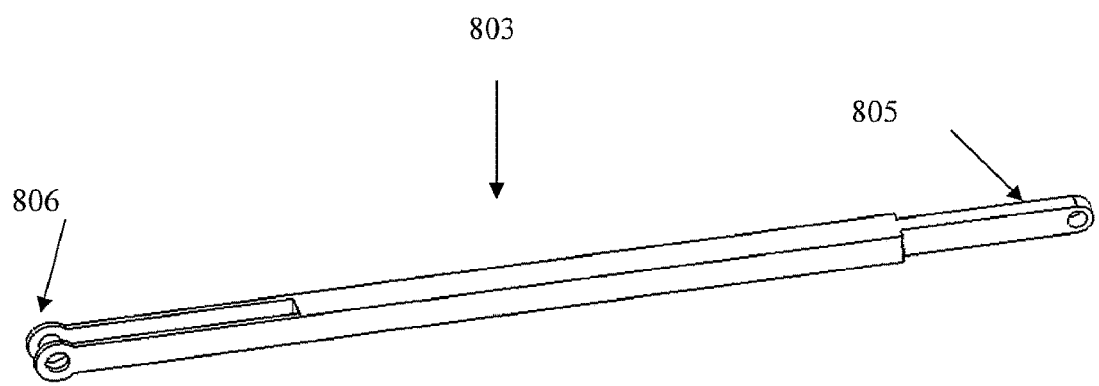
FIG. 12A-E illustrates the different components of the staple gun.
Figure 12B:
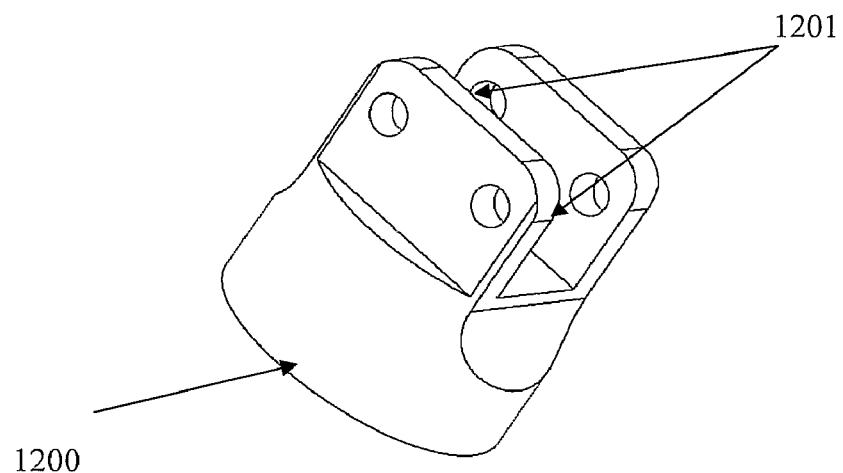
Figure 12C:
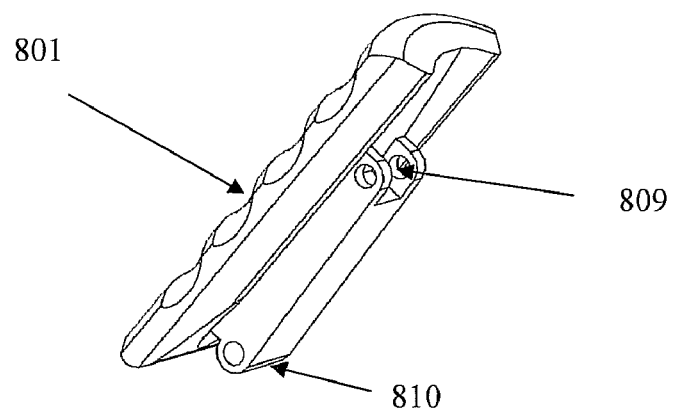
Figure 12D:
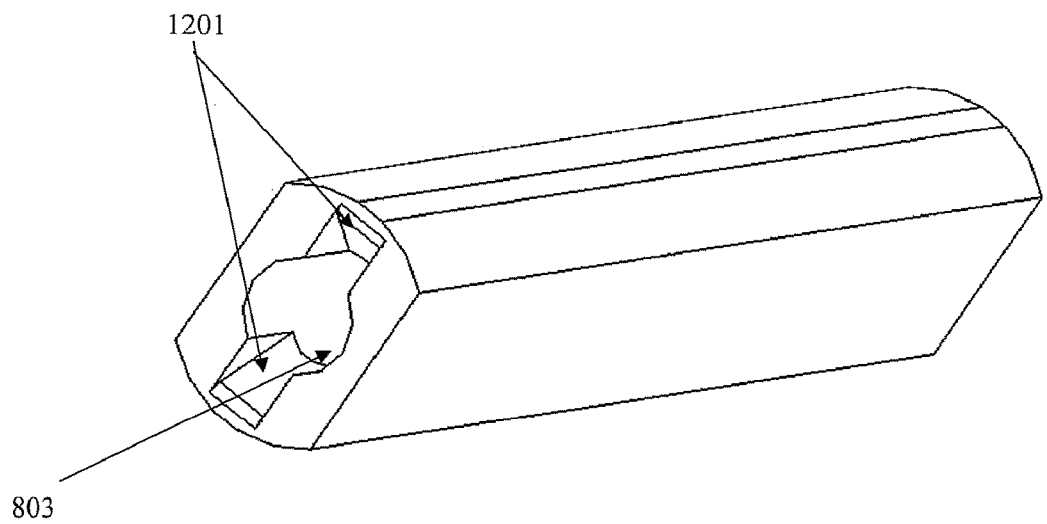
Figure 12E:
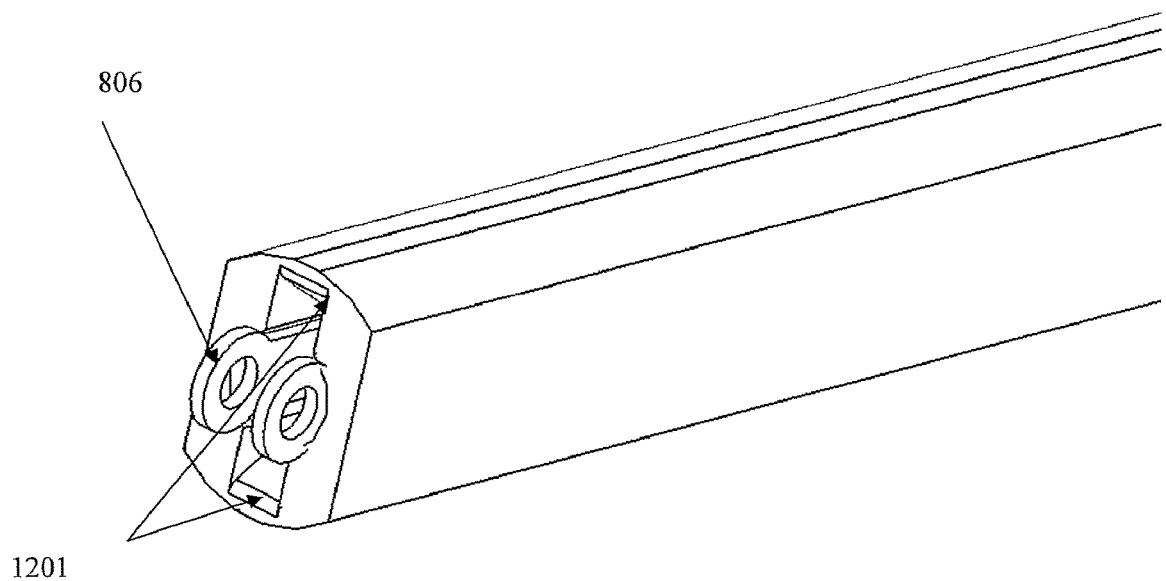
Figure 13:
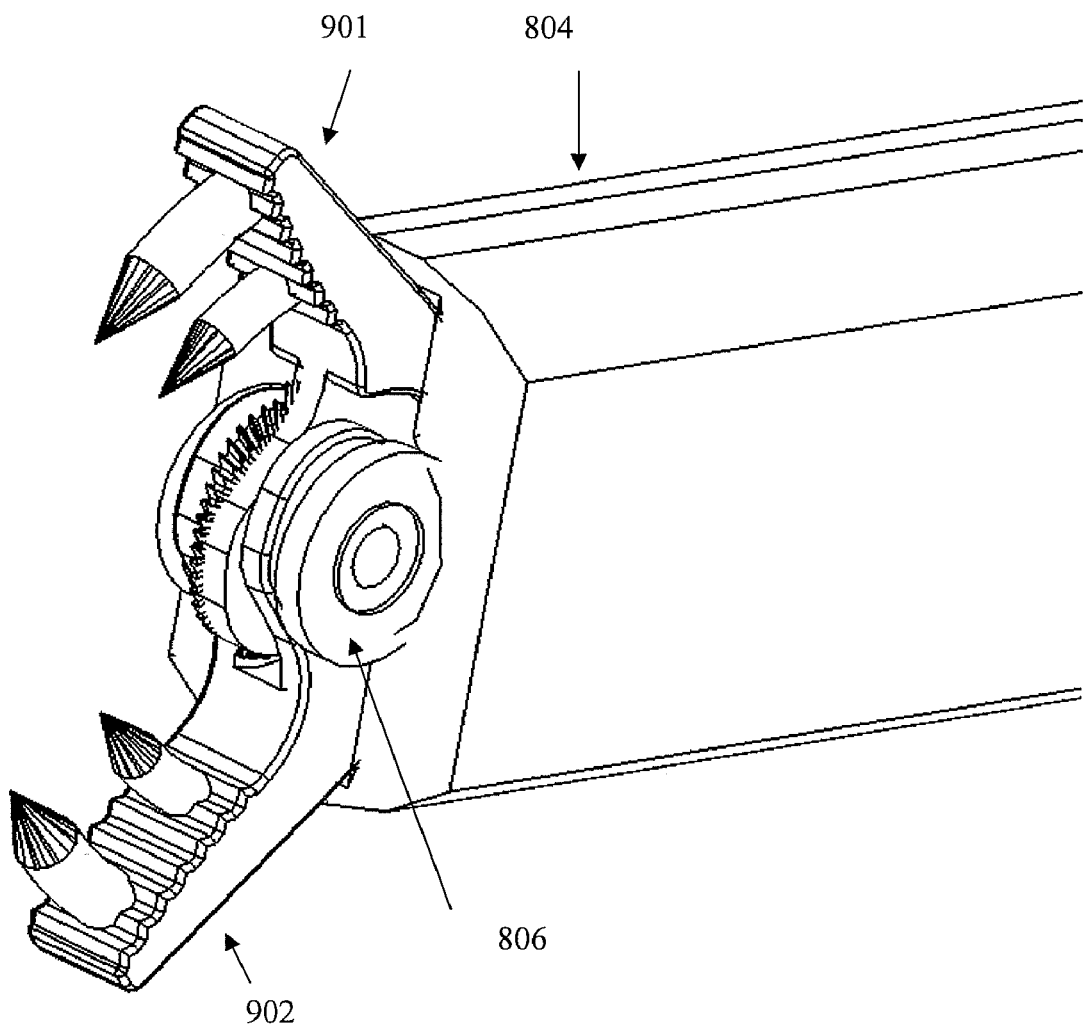
FIG. 13 illustrates the drive and insertion mechanism of the staple.

FIGS. 11-13 illustrate the different components of the staple gun 800 and staple 900 in a detailed manner. The mechanism of action of the staple gun 800 includes engaging the staple 900 in the action end 806 of the drive rod 803 and resting in the staple guide chamfers 1201 (FIGS. 12A-13). When the staple 900 is thus engaged in the staple gun 800, the grip handles 801 are squeezed together, bringing the linkages 802 together (FIGS. 11-12C). This action is transmitted to the force end 805 of the driving rod 803 which moves upwards. This leads to upward movement of the action end 806 of the drive rod 803 in which the staple 900 is nestled, leading to the opposition of the superior and inferior segments 901, 902 of the staple, 900 and the penetration of the pins 907 into the bone. The distance of bone penetration is modulated by the pressure put on the hand grips 801. Hence graded facet joint opposition leading to different degrees of opposition and hence rigidity can be accomplished. The greater the force the greater the opposition. Thus this is a modulated not a static stapling mechanism.

2. The Surgical Method

The surgical steps necessary to practice the present invention will now be described.

The posterior lumbar spine implantation of the BDFT (UBS) screws 100, horizontal mini-plate 600 and IBFD 100a, 100b, 100c can be implanted via previously described posterior lumbar interbody fusion (PLIF) or posterior transforaminal lumbar interbody fusion (TLIF) procedures. The procedure can be performed open, microscopic, closed, tubular or endoscopic. Fluoroscopic guidance can be used with any of these procedures.

After the adequate induction of anesthesia, the patient is placed in the prone position.

A midline incision is made for a PLIF, and one or two parallel paramedian incisions or a midline incision is made for a TLIF. For the PLIF a unilateral or bilateral facet sparing hemi-laminotomy is created to introduce the BDFT (UBS) screws 100, into the disc space after it is adequately prepared. For the TLIF procedure, after a unilateral dissection and drilling of the inferior articulating surface and the medial superior articulating facet, the far lateral disc space is entered and a circumferential discectomy is performed. The disc space is prepared and the endplates exposed.

There are then multiple embodiments to choose from for an intervertebral body fusion. With the first and simplest choice, under direct or endoscopic guidance one. Two or three BDFT screws 100 can be placed. If two screws 100 are placed. One is placed on the right, and one on the left. If three are placed, the additional one can be placed more anterior and midline, such that the three screws 100a, 100b, 100c form a triangulation encompassing the anterior and middle columns of the vertebral bodies. (FIGS. 6B and 6C). Once the screws 100 are placed into the desirable intervertebral body positions, the worm drive screws 105 are turned clockwise which leads to the penetration and engagement of the superior and inferior bi-directional screws 102, 103 into the vertebral bodies above and below. BDFT screws can also be placed in angled positions if desirable (not illustrated). Bone material or alternative intervertebral fusion material can then be packed into the disc space around the BDFTs 100. The casing gear box 101 of the screws prevents subsidence of the vertebral bodies (FIGS. 1A-C). An additional option in the posterior lumbar spine is to place a horizontal mini-plate 600 underneath the thecal sac to prevent bone migration into the nerves. This plate 600 (FIGS. 6A-C) can be slid underneath the thecal sac, and secured to the right and left BDFT (UBS) screws 100. Once set, the plate 600 can be locked down with plate screw caps 606 thereby preventing movement (FIGS. 6A-C).

If further posterior column stability or rigidity is required, unilateral or bilateral, single level or multiple level facet screw stapling 900 can be performed under open, microscopic flouroscopic or endoscopic vision. Radiographic confirmation of staple position is obtained. Calibrated stapling leads to opposition of the facet joints 1000 with incremental degrees of joint opposition. This can lead to variable degrees of posterior column rigidity and/or flexibility (FIGS. 8-13).

The anterior cervical, thoracic and lumbar spine implantation of one, two or three UBS (BDFT) screws 100 can be performed in a similar manner to posterior application. Likewise a horizontal mini-plate 600 can be used to cap two BDFT screws 100. Anterior placement of the three-in-one device (IBFD) 100a, 100b, 100c into the L4/5 and L5/S1 interspaces can be performed on the supine anesthetized patient via previously described open micropscopic or endoscopic techniques. Once the disc space is exposed and discectomy and space preparation is performed, placement of one, two or three BDFT screws 100 with or without a mini-plate 600, or placement of the IBFD 100a, 100b, 100c is identical to that performed for the posterior approach.

The posterior placement of the BDFT screws 100 alone or combined with horizontal mini-plates (two-in-one) 600 or with IBFD 100a, 100b, 100c into the thoracic spine can be performed via previously described transpedicular approaches; open or endoscopic. The anterior placement of the IBFD (three-in-one) into the thoracic spine can be accomplished via a trans-thoracic approach. Once disc space exposure is obtained via either approach, all of the above mentioned embodiments can be inserted. Engagement of the devices is identical to what was mentioned above.

For anterior placement of the cervical embodiments of the BDFT screw(s) 100 with or without the horizontal cervical mini-plate 600, and the IBFD 100a, 100b, 100c embodiment, the anterior spine is exposed in the anesthetized patient as previously described for anterior cervical discectomies. Once the disc space is identified, discectomy is performed and the disc space prepared. Implantation and engagement of all devices is identical to that described for the anterior lumbar and thoracic spines.

The present invention may provide an effective and safe technique that overcomes the problems associated with current tanspedicular-based thoracic and lumbar fusion technology, and with current vertical cervical plating technology, and for many degenerative stable and unstable spine diseases, and could replace many pedicle screw-based and anterior vertical-plate based instrumentation in many but not all degenerative spinal conditions. Calibrated facet joint screw staples 900 can facilitate flexible fusions and could replace current static trans-facet screws.

To our knowledge there has not been any other previously described bi-directional screw 100 for use in the spine, other joints, or for any commercial or carpentry application. The bi-directional screw 100 described herein may indeed have applications in general commercial, industrial and carpentry industries. To our knowledge the description of zero to subzero profile anterior or posterior horizontal spinal plates which traverse the diameter of the disc space has not been previously described. To our knowledge an intervertebral three-in-one construct 100a, 100b, 100c has not been previously reported. To our knowledge calibrated facet joint staples 900 have not been previously described.

We claim:

1. A bidirectional fixating intervertebral implant system, the system comprising:
   at least one implant body comprising polyether ether ketone (PEEK) configured to act to reduce subsidence of a disc space between first and second vertebral bodies when implanted into the disc space, the implant body having a first vertebral body-facing surface having a first set of ridges and an opposing second vertebral body-facing surface having a second set of ridges configured for engaging the first and second vertebral bodies, wherein the first vertebral body-facing surface defines a first anchor opening and wherein the second vertebral body-facing surface defines a second anchor opening, wherein the implant body has a body top surface, a body bottom surface, and first and second body side surfaces that combine to define a body perimeter extending around the implant body between the first and second vertebral body-facing surfaces;
   a perimeter enclosure comprising titanium and extending around and connected to the body perimeter of the implant body, wherein the perimeter enclosure surrounds and covers at least part of the body top surface, the body bottom surface, and the first and second body side surfaces while exposing the first and second vertebral-body facing surfaces so as to allow the first and second vertebral body-facing surfaces to abut the first and second vertebral bodies when the implant system is implanted in the disc space, wherein the implant body and the perimeter enclosure are sized to fit within the disc space when the implant body and the perimeter enclosure are combined and implanted in the disc space, wherein the perimeter enclosure defines at least one tool hole extending through the perimeter enclosure to the top surface of the implant body;
   a first anchor sized and configured to extend through the first anchor opening from a position that is internal to the at least one implant body to a position that is external to the at least one implant body, wherein the first anchor has a first shaft portion sized and configured to extend through the first anchor opening and a first vertebral body engagement portion extending laterally outward from the first shaft portion in multiple directions to engage the first vertebral body when the implant system is positioned in the disc space; and
   a second anchor sized and configured to extend through the second anchor opening from a position that is internal to the at least one implant body to a position that is external to the at least one implant body, wherein the second anchor has a second shaft portion sized and configured to extend through the first anchor opening and a second vertebral body engagement portion extending laterally outward from the second shaft portion in multiple directions to engage the second vertebral body when the implant system is positioned in the disc space.

2. The implant system of claim 1, wherein the first and second anchors comprise first and second screws and the first and second vertebral body engagement portions comprise first and second screw threads.

3. The implant system of claim 1, wherein the first vertebral body engagement portion extends entirely around the first shaft and the second vertebral body engagement portion extends entirely around the second shaft.

4. The implant system of claim 1, wherein the first vertebral body engagement portion spirals around the first shaft and the second vertebral body engagement portion spirals around the second shaft.

5. The implant system of claim 1, wherein the first and second vertebral body engagement portions of the first and second anchors comprise planes.

6. The implant system of claim 1, wherein the first and second anchors have pointed tips.

7. The implant system of claim 1, wherein the first vertebral body engagement portion is angled with respect to the first vertebral body-facing surface and the second vertebral body engagement portion is angled with respect to the second vertebral body-facing surface.

8. The implant system of claim 1, wherein the at least one tool hole is aligned with a hole in the top surface of the implant body.

9. The implant system of claim 1, wherein the implant system defines a plurality of slots extending through the implant system for bone fusion material.

10. The implant system of claim 1, and further comprising:
    a third anchor having a third shaft portion and a third vertebral body engagement portion extending laterally outward from the third shaft portion in multiple directions to engage the first vertebral body when the implant system is positioned in the disc space;
    a fourth anchor having a fourth shaft portion and a fourth vertebral body engagement portion extending laterally outward from the fourth shaft portion in multiple directions to engage the second vertebral body when the implant system is positioned in the disc space;
    wherein the first anchor is positioned opposite of the second anchor and the third anchor is positioned opposite of the fourth anchor, wherein the implant system defines first, second, and third slots extending through the implant system for bone fusion material with the second slot extending through the implant system at a location between the first and third anchors and between the second and fourth anchors.

11. The implant system of claim 1, wherein the first anchor is positioned opposite of the second anchor, wherein the first shaft portion extends from the implant system in a first direction and the second shaft portion extends from the implant system in a second direction with the first direction being opposite of the second direction, wherein the implant system defines a plurality of slots extending through the implant system for bone fusion material, wherein the at least one tool hole extending through the perimeter enclosure to the top surface of the implant body comprises a plurality of tool holes extending through the perimeter enclosure to the top surface of the implant body.

12. The implant system of claim 1, wherein the perimeter enclosure comprises a superior portion positioned nearer the first vertebral body-facing surface and an inferior portion positioned nearer the second vertebral body-facing surface.

13. The implant system of claim 1, wherein a first potion of the perimeter enclosure extends along at least part of the body perimeter of the implant body and has a first superior edge and a first inferior edge, wherein a second potion of the perimeter enclosure extends along at least part of the body perimeter of the implant body and has a second superior edge and a second inferior edge, wherein the first inferior edge of the first portion faces the second superior edge of the second portion, wherein the first superior edge of the first portion faces the first vertebral body when the implant system is implanted in the disc space, and where the second inferior edge of the second portion faces the second vertebral body when the implant system is implanted in the disc space.

14. The implant system of claim 1, wherein the first inferior edge of the first portion abuts the second superior edge of the second portion.

15. The implant system of claim 1, and further comprising means for extending the first and second anchors.

16. The implant system of claim 1, wherein the implant system is sized to cover an entire cross-sectional area of the disc space.

17. The implant system of claim 1, wherein the at least one implant body comprises a plurality of implant bodies positioned inside the perimeter enclosure.

18. A method of operating the implant system of claim 1, the method comprising:
inserting the implant body and the perimeter enclosure into the disc space between the first and second vertebral bodies, wherein the implant body is positioned in the perimeter enclosure while being inserted and wherein the first and second anchors do not extend out of the first and second anchor openings during insertion of the implant body and the perimeter enclosure into the disc space;
extending the first anchor into the first vertebral body with the first vertebral body engagement portion cutting into and engaging the first vertebral body and with part of the first shaft portion retained in the implant body, wherein the first anchor is extended into the first vertebral body after the implant body and the perimeter enclosure are positioned in the disc space; and
extending the second anchor into the second vertebral body with the second vertebral body engagement portion cutting into and engaging the second vertebral body and with part of the second shaft portion retained in the implant body, wherein the second anchor is extended into the second vertebral body after the implant body and the perimeter enclosure are positioned in the disc space.

19. The method of claim 18, wherein the first and second anchors are positioned internal to the implant body while the implant body is being inserted into the disc space.

20. The method of claim 19, wherein the implant system is inserted into the disc space from an anterior direction and wherein the implant system covers substantially an entire cross-sectional area of the disc space.

* * * * *